United States Patent [19]

Hartman

[11] 4,435,400

[45] Mar. 6, 1984

[54] AMINO AND ALKYLAMINOALKENOATE ESTER DERIVATIVES OF AMINOCHLORONITROPYRAZINE

[75] Inventor: George D. Hartman, Lansdale, Pa.

[73] Assignee: Merck & Co., Inc., Rahway, N.J.

[21] Appl. No.: 399,615

[22] Filed: Jul. 19, 1982

[51] Int. Cl.$^3$ .................. C07D 241/16; C07D 241/20; A01K 31/495

[52] U.S. Cl. ..................................... 424/250; 544/409

[58] Field of Search ......................... 544/409; 424/250

[56] References Cited

U.S. PATENT DOCUMENTS 3,660,397  5/1972  Jones et al. ........................ 544/409

FOREIGN PATENT DOCUMENTS 1232756  5/1971  United Kingdom ................ 544/409

OTHER PUBLICATIONS

Cragoe, et al.; "N-Amidino-3 amino-5 Substituted-6 Halopyrazine Carboxamides," *J. Med. Chem.:10*, pp. 66–75, 1967.
Chin et al., "Screening . . . Radiosensitizers," *Chem. Abst.*, 89:20966z.
Anderson, R. F. et al., "Radiosensitization . . . by Nitropyridium Compounds," *Br. J. Cancer*, 37, Suppl. III, pp. 103–106 (1978).
Rauth et al., "In Vitro Testing . . . Radiosensitizers," *Chem. Abst.* 85:40894f (1976).
Denekamp et al., "Hypoxic Cells Radiosensitizers," *Chem. Abst.* 82:93112w.
Ainsworth et al., *Can. J. Biochem.*, 10156, pp. 457–461 (1978).
Adams et al., *Lancet*, pp. 186–188, Jan. (1976).
Olive, P. L., *Cancer Res.*, 39, pp. 4512–4515, Nov. (1979).

*Primary Examiner*—Donald G. Daus
*Assistant Examiner*—G. Hendricks
*Attorney, Agent, or Firm*—Thomas E. Arther; Mario A. Monaco

[57] ABSTRACT

The present invention relates to aminoalkenoate ester derivatives of 2-amino-5-chloro-3-nitropyrazine useful as sensitizers of hypoxic tumor cells to therapeutic radiation. It also relates to the process of preparing such compounds by reaction of 2-amino-5,6-dichloro-3-nitropyrazine with an amino or alkylamino substituted $\alpha,\beta$-unsaturated alkenoate ester. In addition the application relates to pharmaceutical compositions containing such compounds and to methods of treatment comprising administering such compounds to patients undergoing radiation treatment to enhance the effectiveness of such treatment by sensitizing hypoxic tumor cells to therapeutic radiation.

8 Claims, No Drawings

AMINO AND ALKYLAMINOALKENOATE ESTER DERIVATIVES OF AMINOCHLORONITROPYRAZINE

BACKGROUND OF THE INVENTION

At the present time certain other unrelated compounds are in experimental clinical use as radiosensitizers. However, these compounds—for example mitronidazole and misonidazol—suffer from the drawback that they also cause neurotoxicity which limits their usefulness.

It is an object of the present invention to prepare new substituted pyrazines which are highly effective in sensitizing hypoxic tumor cells to the therapeutic effect of radiation treatment but which do not cause neurotoxic effects in the patient being treated.

It is a further object of the present invention to provide a process for the preparation of such novel pyrazine compounds.

It is a still further object to provide pharmaceutical compositions of such compounds containing the novel pyrazine compounds and a non-toxic pharmaceutically acceptable carrier.

DESCRIPTION OF THE INVENTION

The compounds of the present invention which are useful as radiation sensitizers are amino-5-N-substituted aminoalkenoate ester or derivatives of 2-amino(or alkenoylamino)-5-chloro-3-nitropyrazines.

More specifically this invention relates to substituted derivatives of aminoalkenoate esters of 2-amino(or alkanoylamino)-5-chloro-3-nitropyrazine compounds having the formula:

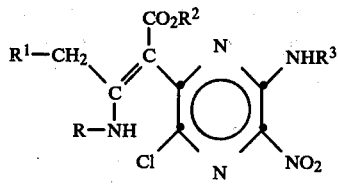

where R, $R^1$ and $R^2$ may be the same or different and are each selected from the group consisting of H, $C_{1-6}$alkyl, $C_{1-6}$mono-or polyhydroxyalkyl, or $C_{1-6}$aminoalkyl and $R^3$ is selected from the group consisting of H and lower $C_{1-6}$alkanoyl radicals and to acid addition salts thereof.

Still more specifically the present invention relates to compounds having the formula

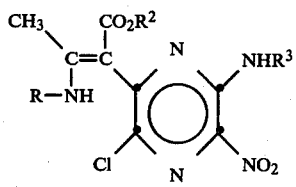

wherein R, $R^2$ and $R^3$ are defined as hereinabove and acid addition salts thereof formed by reaction of the above amino pyrazine with an equivalent amount of a strong mineral acid such as hydrochloric, hydrobromic, sulfuric and phosphoric acids.

In general the compounds of the subject invention are prepared in accordance with the following reaction scheme

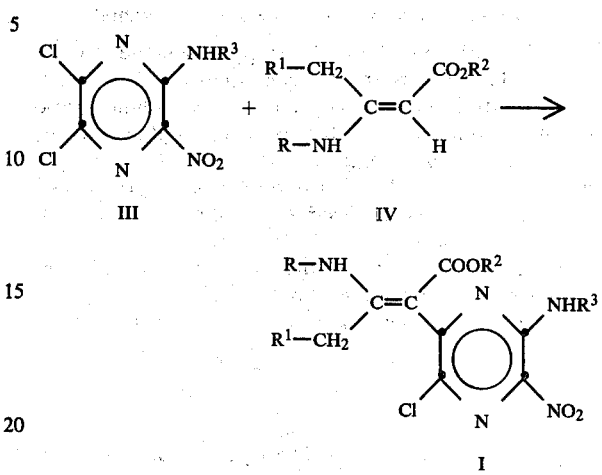

wherein R, $R^1$, $R^2$ and $R^3$ are as previously defined as illustrated hereinabove. The reaction of the dichloronitropyrazine III with the aminocrotonate IV is preferably carried out in the presence of an acid neutralizing agent; for example a tertiary amine such as triethylamine. The aminocrotonate reactant is preferably present in approximately a 5–10% molar excess over the chloronitropyrazine. The reagents are first mixed and then preferably heated in a suitable solvent such as lower alcohols, ether, DMF, or DMA to a temperature of 20°–80° C. for a period of from 0.5 to 24 hours. In addition to the reagents and the solvent it is generally preferred to carry out the reaction in the presence of at least an equimolar amount of an organic base. Tertiary amines such as triethylamine and pyridine are preferred. The progress of the reaction is followed by the use of thin layer chromatography.

As indicated hereinabove acid addition salts of compounds of Formula I or II may be prepared by mixing a selected compound of Formula I or II with an equimolar amount of a strong mineral acid in a solvent for the reactants at a temperature of 0° to 50° C. Solvents preferred are lower alkanols such as methanol, ethanol, isopropanol. The salt is precipitated from the alcoholic solution, filtered, washed with a minimal amount of cold alcohol and air dried.

The starting materials for the preparation of the compounds of our invention are prepared from known materials in the following manner.

Preparation of 5,6-Dichloro-3-nitropyrazinamine and N-acetyl derivatives thereof:

Preparation of 5,6-dichloro-3-nitropyrazinamine

To 450 ml concentrated sulfuric acid cooled to 10° is added 50.0 g (0.2 m) 3-amino-5,6-dichloropyrazine carboxylic acid. To this solution cooled to 0°–5°, is added a cold solution of 15 ml fuming sulfuric acid in 15 ml fuming nitric acid dropwise over 15 minutes. The reaction mixture is stirred at 0°–5° for 2 hours and then at ambient temperature for 2 hours. The reaction mixture is then poured onto ice and the yellow solid is collected. This solid is taken up in ethyl acetate, washed twice with saturated sodium carbonate solution and then the solution is filtered through a pad of silica gel. The resulting solution is evaporated in vacuo to afford 35 g of 5,6-dichloro-3-nitropyrazinamine, m.p. 169°–170° C.

STEP B: Preparation of N-(5,6-dichloro-3-nitropyrazin-2-yl)acetamide

To 1.0 g of 5,6-dichloro-3-nitropyrazinamine in 15 ml acetyl chloride under nitrogen atmosphere at room temperature is added 0.84 g anhydrous sodium bicarabonate. The reaction mixture is then stirred and heated at reflux for 4 days. Excess acetyl chloride is then removed in vacuo and the residue is chromatographed on silica gel. The desired product is eluted from the column with chloroform.

The aminocrotonates IV used as reagents in the preparation of the compounds of our invention are prepared from known compounds in the following manner.

Preparation of Aminocrotonates

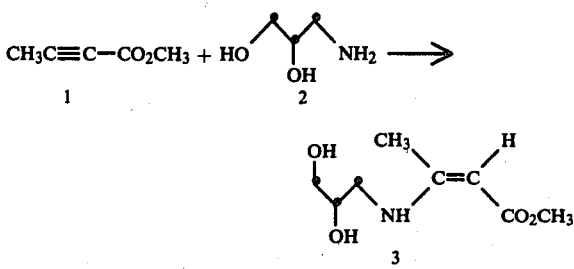

Preparation A: Methyl 3-(2,3-dihydroxypropyl)amino-2-butenoate (3)

To 5.0 g (0.051 m) methyl 2-butynoate in 25 ml absolute ethanol was added 5.0 g (0.055 m) 2,3-dihydroxypropylamine. This solution was heated at 75°–80° for 18 hours and the solvent was then removed at reduced pressure. The residue oil was chromatographed on silica gel, eluting with 10% methanol/chloroform to afford the desired product as a white solid, m.p. 109°–111°. The yield was 5.6 g (59%).

Preparation B: Methyl 3-(1-deoxy-1-arabinyl)amino-2-butenoate (4)

To 4.9 g (0.05 m) methyl-2-butynoate in 100 ml dry dimethylsulfoxide was added 6.5 g (0.043 m) 1-amino-1-deoxyarabinitol in one portion. The resulting solution was heated at 70°–75° for 16 hours. The solvent was then removed in vacuo to give a white solid that was triturated with Et₂O. This suspension was filtered to afford the desired product as a white powder, m.p. 162°–4°.

The method of treatment of human patients or domestic animals undergoing radiation treatment of malignant disease processes employs the compounds of the present invention in pharmaceutical compositions that are administered orally or parenterally, preferably intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface, approximately equivalent to a dosage of 6 to 100 mg/kg of patient body weight as set forth in the "Nelson Textbook of Pediatrics" Eleventh Edition (1979) p. 31, edited by Vaughan, McKay, Behrman, and Nelson.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs are preferred.

Capsules or tablets containing from 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention.

EXAMPLE 1

Methyl 2-[6-amino-3-chloro-5-nitropyrazin-2-yl]-3-(2,3-dihydroxypropyl)amino-2-butenoate (6)

To 75 ml of isopropanol is added 3.3 g (0.017 m) methyl 3-(2,3-dihydroxypropyl)amino-2-butenoate (3), 4.18 g (0.02 m) 5,6-dichloro-3-nitropyrazinamine (5), and 2.0 g (0.02 m) triethylamine. This solution is heated at 60°–65° for two days. The reaction mixture is then stripped on the rotary evaporator and the residue chromatographed on silica gel eluted with 12% methanol/chloroform. Material with $R_f=0.5$ is collected and after crystallization from acetonitrile the desired product is an orange solid, m.p. 184°–186° (dec).

EXAMPLE 2

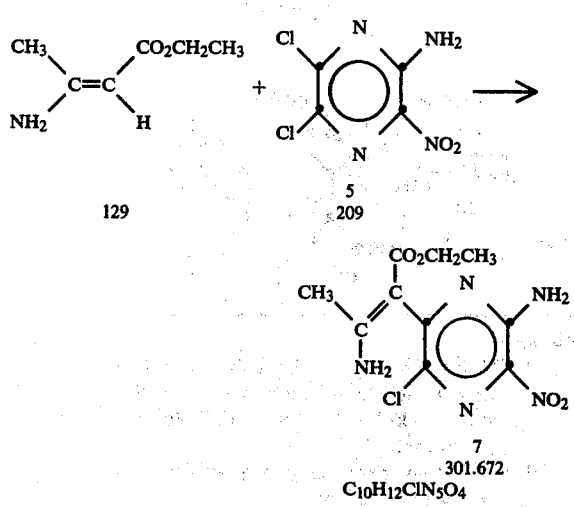

Ethyl-2-(6-amino-3-chloro-5-nitropyrazin-2-yl)-3-amino-2-butenoate (7)

To 50 ml of isopropanol is added 2.0 g (0.0096 m) 5, 3.0 g (0.02 m) ethyl 3-aminocrotonate and 1.0 g (0.01 m) triethylamine. This solution is heated at 65°–70° for seven days. The solvent is then stripped on the rotary evaporator and the residue is chromatographed on silica gel eluted with 1% methanol/chloroform. Material with $R_f=0.5$ with the solvent system is isolated and crystallized from 1:1 methanol/chloroform to give 0.9 g of 7 as a tan solid, m.p. 162°–3°.

EXAMPLE 3

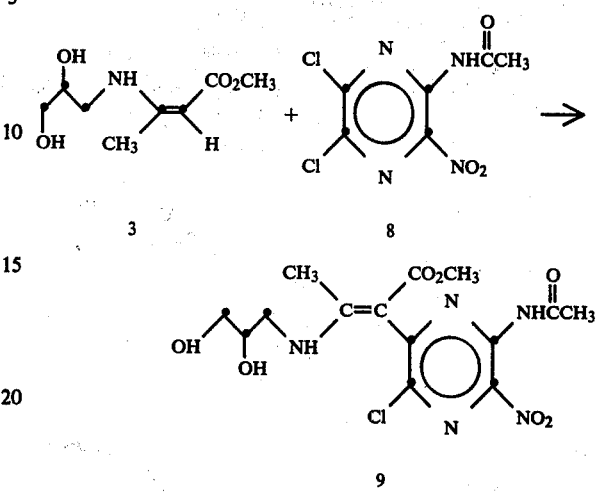

Methyl 3-(2,3-dihydroxypropyl)amino-2-[3-chloro-6-(methylcarbonyl)amino-5-nitropyrazin-2-yl]-2-butenoate (9)

To 50 ml isopropanol is added 2.0 g (0.008 m) N-(5,6-dichloro-3-nitropyrazinyl)acetamide (8), 1.32 g (0.007 m) methyl 3-(2,3-dihydroxypropyl) amino-2-butenoate (3), and 0.81 g (0.008 m) triethylamine. This dark solution is stirred at room temperature for five days. The solvents are then removed on the rotary evaporator and the residue is chromatographed on silica gel and is eluted with 8% methanol/chloroform. Material with $R_f=0.5$ is collected. This material is a reddish brown solid and is further purified by high pressure liquid chromatography to afford 9 as a brown solid, m.p. 70°–73°.

EXAMPLE 4

When the procedure of the preceding example is repeated using equivalent amounts of the following hydroxyalkyl aminocrotonate reactants, the indicated products are obtained.

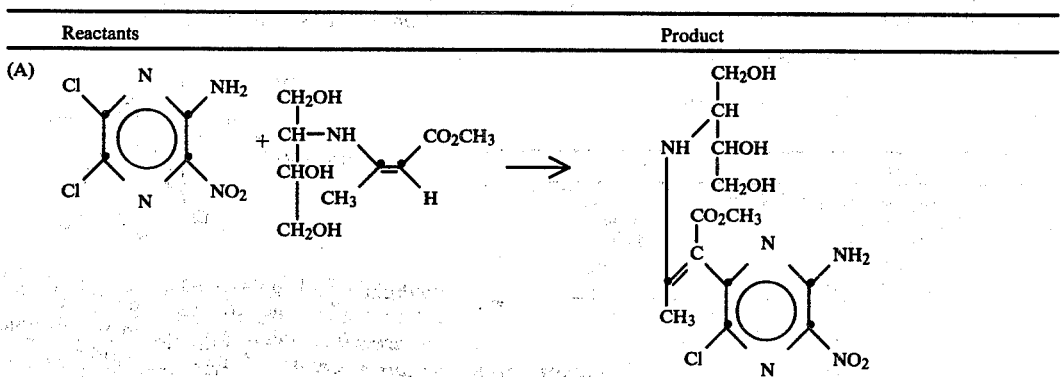

| Reactants | Product |
| --- | --- |

(A)

-continued

| Reactants | Product |
|---|---|
| (B) 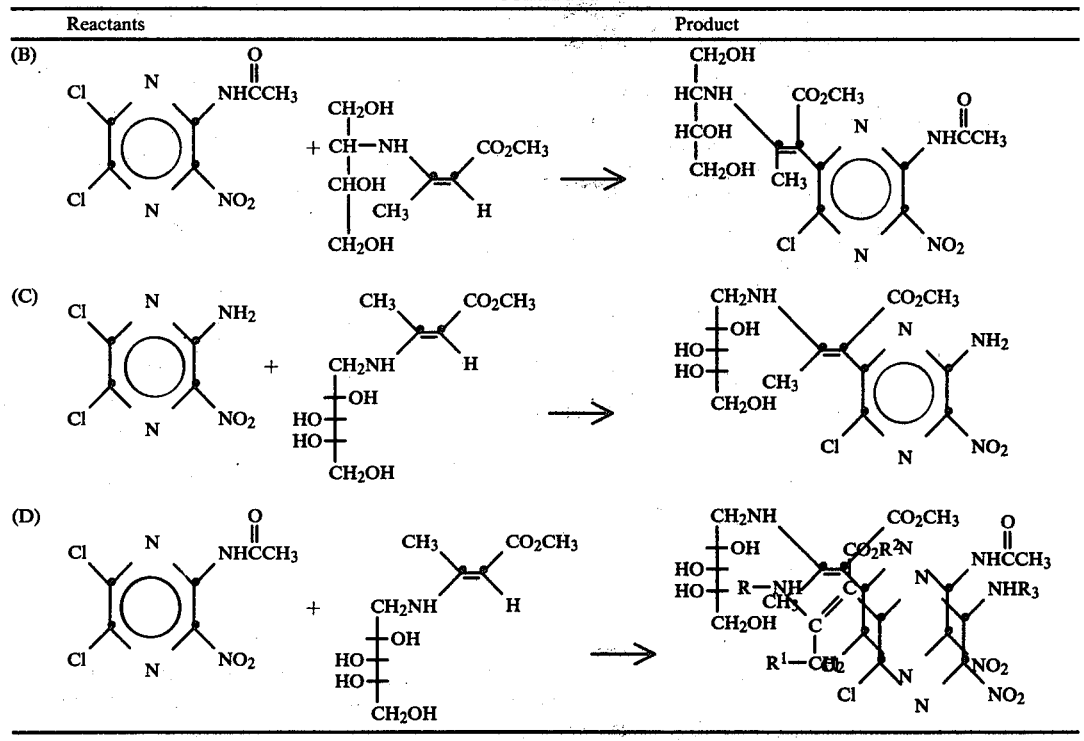 | |
| (C) | |
| (D) | |

EXAMPLE 11

Sterile Isotonic Solutions for Injection

Suitable formulations for injection are prepared by dissolving each of the compounds of Examples 1–4 inclusive in isotonic solution in a concentration of about 1 mg/ml and sterilizing the resulting solution. It is suitable for intravenous injection.

EXAMPLE 12

Capsules

Suitable formulations for oral administration are prepared by filling appropriately sized capsules individually with 25 and 50 mg portions of each of the compounds produced in accordance with Examples 1–4 inclusive.

EXAMPLE 13

Tablet Formulation

| Ingredients | Amount |
|---|---|
| Product of Examples 1–4 | 25 mg |
| Calcium phosphate | 120 mg |
| Lactose | 50 mg |
| Starch | 23 mg |
| Magnesium Stearate | 1 mg |

What is claimed is:

1. An aminoalkenoate ester of 2-amino(or alkanoylamino)-5-chloro-3-nitropyrazine compound having the formula:

where
R, $R^1$ and $R^2$ may be the same or different and are each selected from the group consisting of hydrogen, $C_{1-6}$alkyl, $C_{1-6}$ mono-to tetrahydroxyalkyl, or $C_{1-6}$aminoalkyl;
$R^3$ is selected from the group consisting of hydrogen and lower $C_{1-6}$alkanoyl;
and acid addition salts thereof.

2. A compound according to claim 1 wherein $R^3$ is hydrogen.

3. A compound according to claim 1 wherein $R^3$ is lower alkanoyl of from 1–6 carbon atoms.

4. A compound according to claim 2 which is methyl 2-[6-amino-3-chloro-5-nitropyrazin-2-yl]-3-(2,3-dihydroxypropyl)amino-2-butenoate.

5. A compound according to claim 2 which is ethyl 2-(6-amino-3-chloro-5-nitropyrazin-2-yl)-3-amino-2-butenoate.

6. A compound according to claim 3 which is methyl 3-(2,3-dihydroxypropyl)amino-2-[3-chloro-6-(methylcarbonyl)amino-5-nitropyrazin-2-yl]-2-butenoate.

7. A method for enhancing the therapeutic effect of radiation which comprises administering to a patient in need of such radiation treatment an effective amount of a compound of the formula:

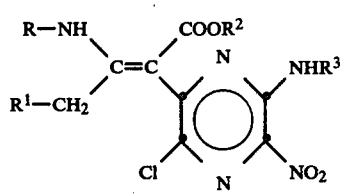

wherein R, $R^1$, $R^2$ and $R^3$ are as defined in claim 1.

8. A pharmaceutical composition for enhancing the therapeutic value of radiation which consists of an effective amount of the compound of claim 1 and a non-toxic pharmaceutically acceptable carrier.

* * * * *

UNITED STATES PATENT AND TRADEMARK OFFICE
CERTIFICATE OF CORRECTION

PATENT NO. : 4,435,400

DATED : March 6, 1984

INVENTOR(S) : George D. Hartman

It is certified that error appears in the above-identified patent and that said Letters Patent is hereby corrected as shown below:

In Column 7, Claim 1, after "having the formula:", insert the formula below --

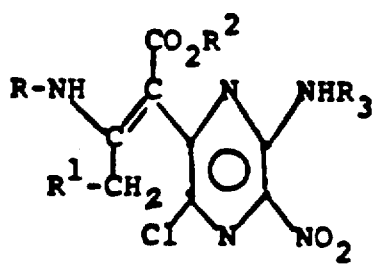

UNITED STATES PATENT AND TRADEMARK OFFICE
CERTIFICATE OF CORRECTION

PATENT NO. : 4,435,400            Page 2 of 2

DATED : March 6, 1984

INVENTOR(S) : George D. Hartman

It is certified that error appears in the above-identified patent and that said Letters Patent is hereby corrected as shown below:

In Column 8, under "Product", in structural formulation (D), 3rd structure, lower right -- should be corrected to read:

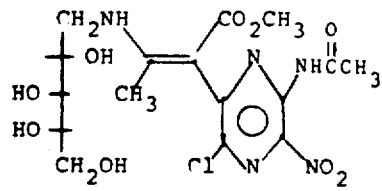

[SEAL]

Signed and Sealed this

Twenty-second Day of May 1984

Attest:

GERALD J. MOSSINGHOFF

*Attesting Officer*      *Commissioner of Patents and Trademarks*